(12) United States Patent
Crihan

(10) Patent No.: US 6,455,013 B1
(45) Date of Patent: Sep. 24, 2002

(54) STERILIZATION OF MEDICAL MATERIALS IN AN IMPROVED IRRADIATING UTILITY

(76) Inventor: Ioan Crihan, 417 E. 64th St. #4G, New York, NY (US) 10021

( * ) Notice: Subject to any disclaimer, the term of this patent is extended or adjusted under 35 U.S.C. 154(b) by 0 days.

(21) Appl. No.: 09/826,933

(22) Filed: Apr. 6, 2001

Related U.S. Application Data

(62) Division of application No. 08/766,138, filed on Dec. 17, 1986, now Pat. No. 6,242,664.

(51) Int. Cl.[7] ................................................. B01J 19/00
(52) U.S. Cl. .................................... 422/186; 422/186.05
(58) Field of Search ........................... 422/186, 186.05; 588/227; 204/158.15, 158.2; 210/748; 426/240

(56) References Cited

U.S. PATENT DOCUMENTS 4,151,419 A * 4/1979 Morris et al. .................. 378/69

* cited by examiner

Primary Examiner—Nathan M. Nutter
Assistant Examiner—Thao Tran

(57) ABSTRACT

A method and equipment for accomplishing the rapid sterilization of huge quantities of medical and municipal waste materials by exposure to a high dose of radiation energy. The radiation sterilizes organic materials thereby destroying insects, molds, bacteria, viruses and other destructive biological vectors. The equipment includes an improved irradiating facility, namely, either a mobile temporary irradiating chamber, or a fixed temporary irradiation chamber with protective walls capable of being assembled or disassembled. The gear is mounted on suitable transportation means.

8 Claims, 4 Drawing Sheets

STERILIZATION OF MEDICAL MATERIALS IN AN IMPROVED IRRADIATING UTILITY

The present application is a divisional of Ser. No. 08/766,138 filed on Dec. 17, 1986, now U.S. Pat. No. 6,242,664.

SUMMARY OF THE INVENTION

The present invention consists of a method of rapid sterilization, by exposure to high dose of irradiation, of huge quantities of medical waste. The present invention consists also in a method of processing the said type of sterilization at the very place where are located the medical waste to be sterilized, by using either a mobile station or a fixed irradiating chamber with protective walls mounted or dismounted as necessary.

Current method of sterilization, using low doses of energy, has the disadvantage of not permitting the complete sterilization of organic materials, such as the medical waste, at industrial level. At such level, the use of low doses of energy for the sterilization of large quantities of organic material would require a too long period of time. It is one object of this invention to both reduce the time of exposure and to increase considerably the volume of material to be exposed to irradiation, as the best way to use the radiation energy for sterilization at industrial levels.

An exposure to current types of irradiating facilities, mainly of hospital or municipal wastes, would require too much time for transportation and storage. It is, therefore, too costly, and creates other unforerseen problems. It is an object of this invention to avoid, mainly, the problems of transportation and of storage before exposure to irradiation of huge quantities of medical waste. This is accomplished either by transporting a mobile irradiating chamber mounted on a transportation means, or transporting only the components of the protective walls of an irradiating chamber to the place where the medical waste material is generated, and is sterilized at the site. The advantage of such new type of irradiating facilities would consist also in the possibility of the multiplication of both the mobile irradiating chambers and the fixed ones at the locations of the medical waste materials to be sterilized.

DETAILED DESCRIPTION

The present invention consists in a method of rapid sterilization of huge quantities of medical waste materials either in mobile irradiating chambers, or in fixed irradiating chamber, with protective walls to be assembled or disassembled as required.

The mobile and temporary irradiating chamber is built of protective walls mounted on a transportable means, such as a truck, train or ship and, as such, movable to the very locations of the organic material to be sterilized.

The shielding walls of the irradiating chamber consist of assembly of disassembly of panels made of concrete blocks or plates similar in shape, but different in size to the to the conventional lead bricks used for construction of fixed irradiating chambers. Said concrete plates are preferably at least 5 feet in thickness.

The same type of concrete panels could be used to construct a protective shield for a fixed irradiating chamber. Being subject to disassembly, they can be easily constructed or taken apart as needed.

The process of sterilization consists in the following steps. First, the organic materials to be sterilized are distributed onto an endless conveyor system which transports the to-be irradiated organic materials to an irradiating chamber. Secondly, the materials so conveyed are exposed to high doses of irradiation of up to 5,000,000 RAD, emitted from a source of cobalt 60 or cesium 137. The exposure to such a high dose of energy shortens the period of time of irradiation necessary for the sterilization of large quantities of waste organic materials.

Figure 1:
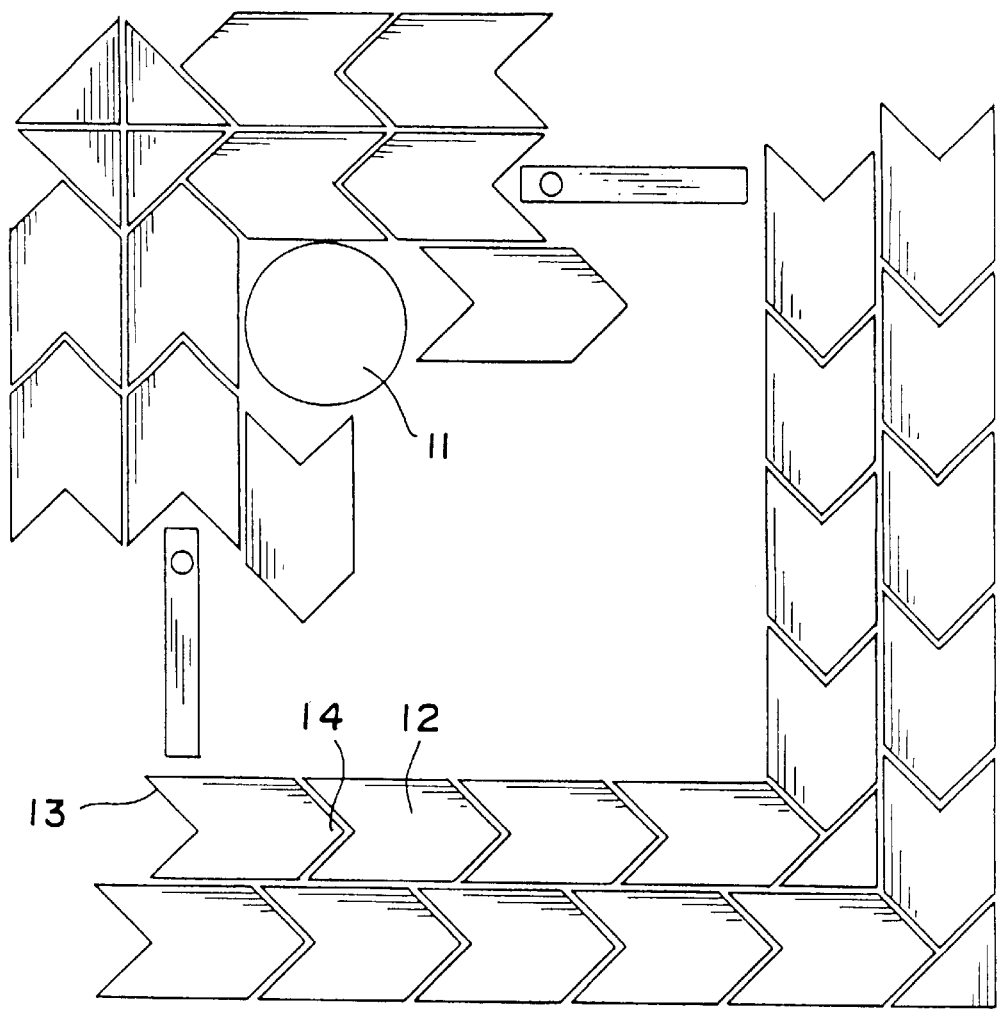
FIG. 1 is a top plan schematic view of the walls for the irradiating chamber.

Attention is directed to FIG. 1 where reference numeral 11 illustrates an irradiation chamber. The chamber 11 is surrounded by at least two rows of concrete blocks 12 which have V-shaped indentations 13 on one side and V-shaped protruberances 14 at each opposite side. The blocks are thereby detailed to interfet or vent as shown, suitable locking engagement means may be used to hold the blocks in assembly, which upon release permits the rapid disassembly.

Figure 2:
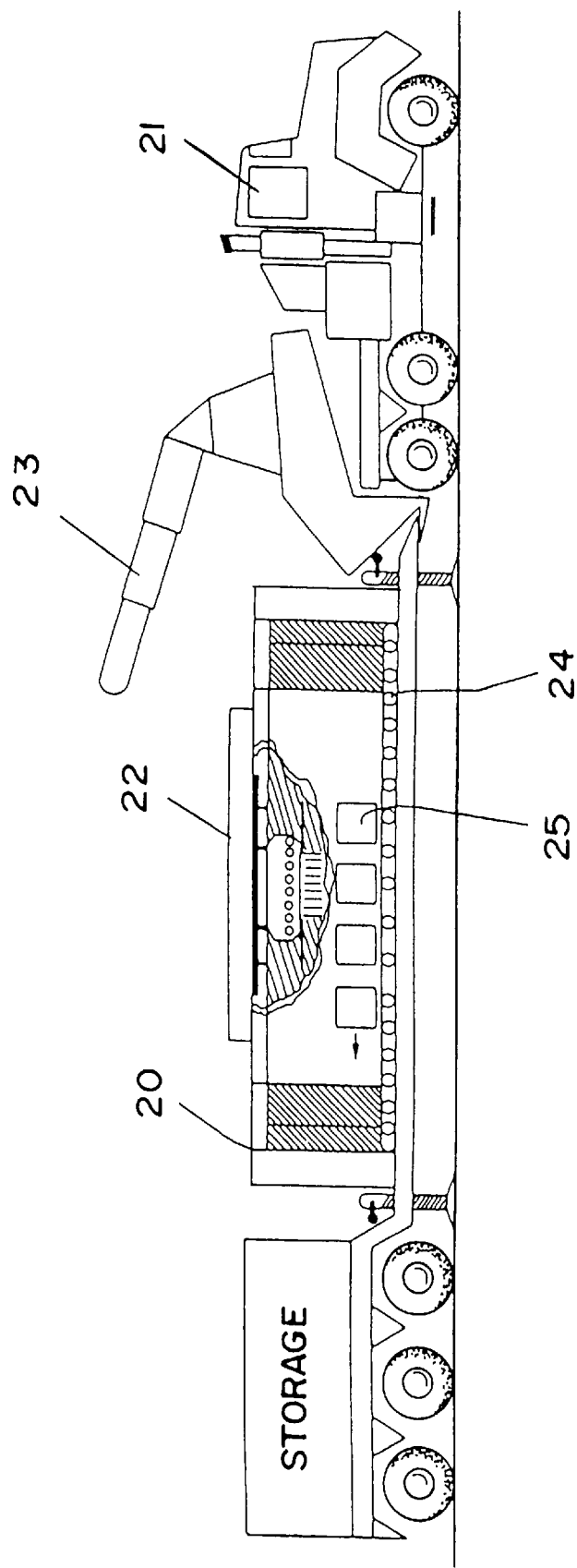
FIG. 2 is a side view showing the transportable irradiating chamber partially fragmented.
Figure 3:
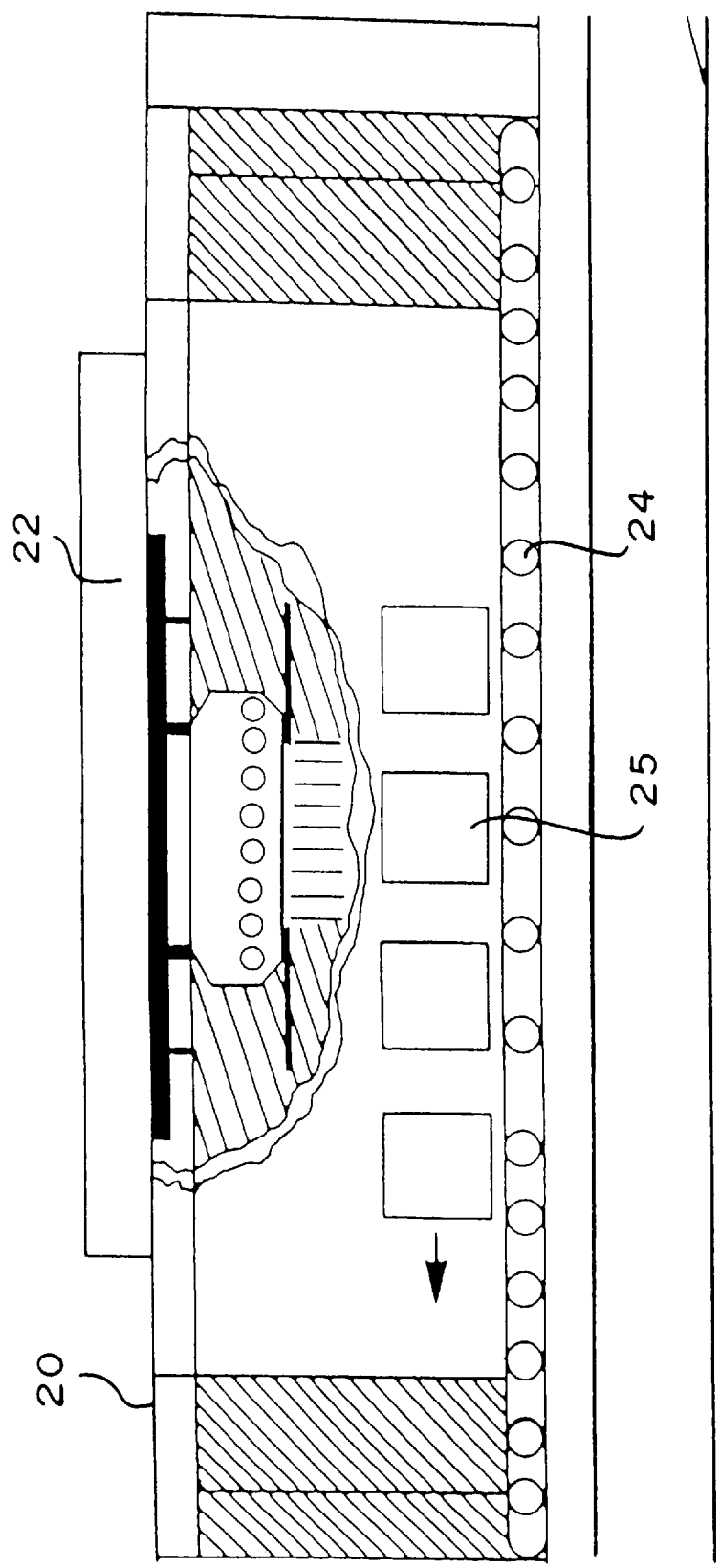
FIG. 3 is an enlarged side view of a portion of FIG. 2.

FIG. 2 shows a transportable trailer 20 having a drawing tractor 21 for bringing the irradiation chamber which is suitably housed in a clad housing. The trailer has a removable protective roof 22 which may be removed by crane 23 in order to load or unload the radioisotopic source. The trailer has a roller conveyor system upon which containers 25 are moved into and out of the irradiation chamber in a timed sequence for a preselected dwell time in the irradiation chamber. The dwell time can be such as to ensure that each container and its contents receiver at least a dosage of 5,000,000 RADs.

Figure 4:
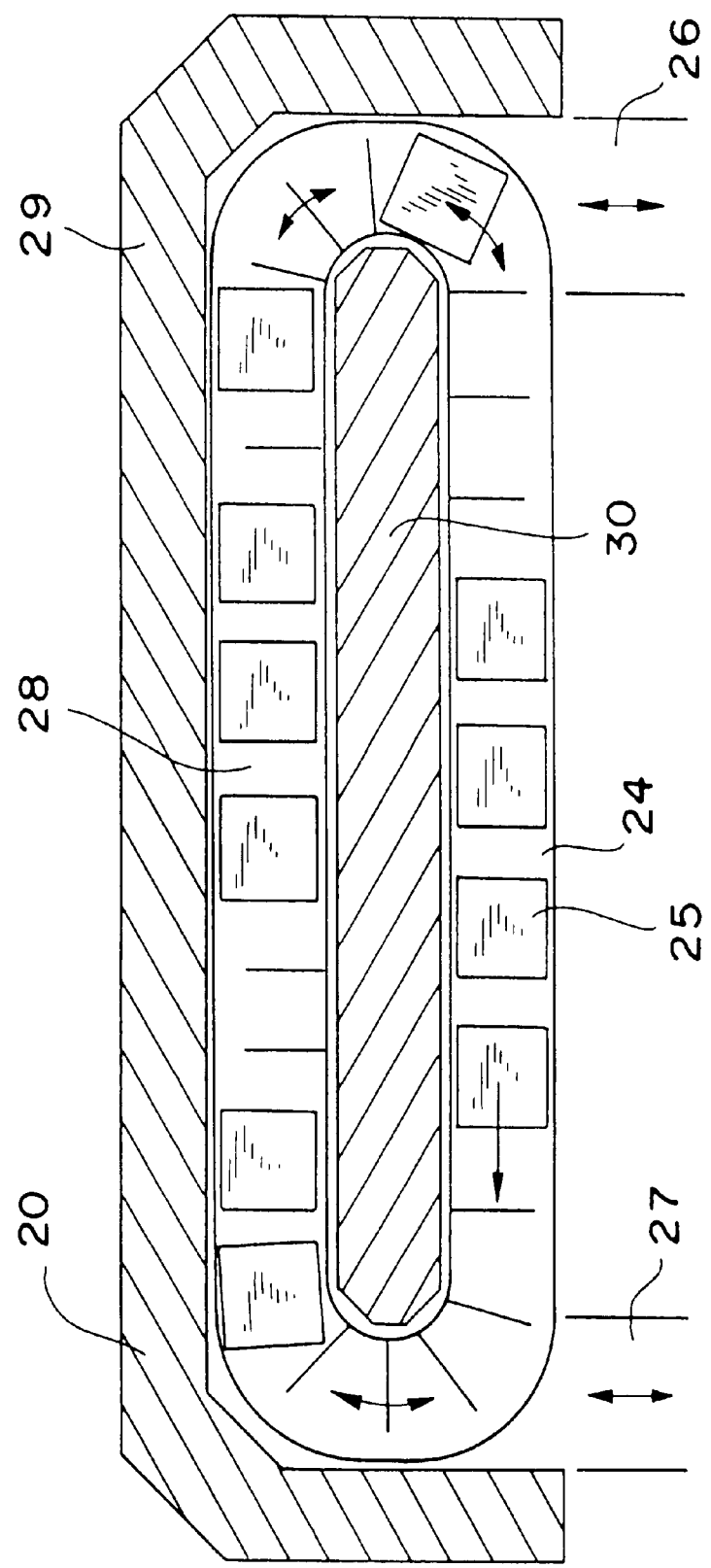
FIG. 4 is a top schematic fragmentary view of FIG. 3.

FIG. 4 shows the containers 25 on the roller conveyor 24 moving into load station 26 and unload station 27. The stations may be reversed. The backside area 28 of the roller conveyor system 24 contains the irradiation source. Suitable shielding walls 29 are provided and a shielding wall 30 interposes the conveyor system 24 which in this embodiment is designed to describe an endless path.

The containers 25 are designed to carry the said waste material to be sterilized into and out of the irradiation chamber having the gamma radiation source consisting of cobalt 60 or cesium 137.

What is claimed is:

1. An apparatus for sterilizing organic material including hospital wastes, biohazardous wastes, sewage, sludge, enzymes of oil, and the harmful bacteria in food products, including a housing, said housing walls being made from interfitting members which are readily assembled and disassembled and including, entirely therewithin, a source of radiation, a conveyor positioned to pass by said source of radiation, and said housing having an ingress opening and an egress opening for introducing material therein onto said conveyor whereby said material is subjected to said source of radiation and thereafter discharged out of said egress opening.

2. The apparatus of claim 1 wherein the housing is disposed on a mobile frame.

3. The apparatus of claim 1 wherein the interfitting members are blocks.

4. The apparatus of claim 1 wherein the interfitting members are plates.

5. The apparatus of claim 1 wherein the convey is endless and is disposed between said ingress opening and said egress opening.

6. The apparatus of claim 5 wherein said ingress opening and said egress opening are the same.

7. The apparatus of claim 1 wherein the source of radiation is about 5,000,000 RAD.

8. The apparatus of claim 7 wherein the material is treated by said radiation source in a single pass thereby.

* * * * *